(12) United States Patent
Patel et al.

(10) Patent No.: US 11,850,436 B2
(45) Date of Patent: *Dec. 26, 2023

(54) METHOD AND APPARATUS FOR TREATMENT OF CARDIOPULMONARY ARREST

(71) Applicants: Vinod Patel, New York, NY (US); Neel Patel, New York, NY (US)

(72) Inventors: Vinod Patel, New York, NY (US); Neel Patel, New York, NY (US)

(*) Notice: Subject to any disclaimer, the term of this patent is extended or adjusted under 35 U.S.C. 154(b) by 102 days.

This patent is subject to a terminal disclaimer.

(21) Appl. No.: 17/521,200

(22) Filed: Nov. 8, 2021

(65) Prior Publication Data

US 2022/0054851 A1   Feb. 24, 2022

Related U.S. Application Data

(63) Continuation of application No. 15/892,864, filed on Feb. 9, 2018, now Pat. No. 11,191,972.

(Continued)

(51) Int. Cl.
*A61H 31/00*  (2006.01)
*A61N 1/39*  (2006.01)
(Continued)

(52) U.S. Cl.
CPC ...... *A61N 1/39044* (2017.08); *A61B 5/02416* (2013.01); *A61B 5/1455* (2013.01); *A61B 5/747* (2013.01); *A61H 3/00* (2013.01); *A61H 9/0078* (2013.01); *A61H 31/006* (2013.01); *A61N 1/3987* (2013.01); *A61H 2011/005* (2013.01); *A61H 2201/0103* (2013.01); *A61H 2201/0192* (2013.01); *A61H 2201/10* (2013.01); *A61H 2201/1238* (2013.01); *A61H 2201/165* (2013.01); *A61H 2201/1621* (2013.01);
(Continued)

(58) Field of Classification Search
CPC .............. A61N 1/39044; A61N 1/3987; A61B 5/02416; A61B 5/1455; A61B 5/747; A61B 5/00; A61H 9/0078; A61H 31/00; A61H 31/006; A61H 2011/005; A61H 2201/0103; A61H 2201/0192; A61H 2201/10; A61H 2201/1238; A61H 2201/1621; A61H 2201/165; A61H 2201/5007; A61H 2201/501; A61H 2201/5043; A61H 2203/0456; A61H 2230/065; A61H 2230/201; A61H 2230/207; G16H 80/00
See application file for complete search history.

(56) References Cited

U.S. PATENT DOCUMENTS

5,490,820 A   2/1996   Schock et al.
5,833,711 A   11/1998  Schneider, Sr.
(Continued)

*Primary Examiner* — Quang D Thanh
(74) *Attorney, Agent, or Firm* — Womble Bond Dickinson (US) LLP (57) ABSTRACT

A cardiopulmonary resuscitation (CPR) device for performing automatic defibrillation and chest compressions on a patient and method for using same. The CPR device having a balloon configured to inflate/deflate, a belt configured to securely strap around a chest of a patient, a pair of electrode pads configured to deliver shock energy from a shock source, and, optionally, a pulse oximeter sensor. The CPR device is in electrical communication with a CPR defibrillator/ECG computer system that is configured to control the CPR device.

21 Claims, 5 Drawing Sheets

Related U.S. Application Data (60) Provisional application No. 62/456,862, filed on Feb. 9, 2017.

(51) Int. Cl.
*A61B 5/00* (2006.01)
*A61B 5/024* (2006.01)
*A61B 5/1455* (2006.01)
*A61H 3/00* (2006.01)
*A61H 9/00* (2006.01)
*A61H 11/00* (2006.01)

(52) U.S. Cl.
CPC ............... *A61H 2201/501* (2013.01); *A61H 2201/5007* (2013.01); *A61H 2201/5043* (2013.01); *A61H 2203/0456* (2013.01); *A61H 2230/065* (2013.01); *A61H 2230/201* (2013.01); *A61H 2230/207* (2013.01)

(56) References Cited

U.S. PATENT DOCUMENTS

| | | | |
|---|---|---|---|
| 11,191,972 B2* | 12/2021 | Patel | A61B 5/747 |
| 2002/0026131 A1 | 2/2002 | Halperin | |
| 2002/0177793 A1 | 11/2002 | Sherman et al. | |
| 2003/0004445 A1 | 1/2003 | Hall et al. | |
| 2004/0162510 A1* | 8/2004 | Jayne | A61H 31/005 |
| | | | 601/44 |
| 2006/0229535 A1* | 10/2006 | Halperin | A61H 31/006 |
| | | | 601/44 |
| 2007/0010765 A1 | 1/2007 | Rothman et al. | |
| 2008/0146975 A1* | 6/2008 | Ho | A61H 31/006 |
| | | | 601/44 |
| 2010/0113990 A1 | 5/2010 | Chang | |
| 2010/0198118 A1 | 8/2010 | Itnati | |
| 2010/0256540 A1 | 10/2010 | Yamashiro et al. | |
| 2015/0272822 A1* | 10/2015 | Wik | A61H 31/007 |
| | | | 601/41 |
| 2016/0213560 A1 | 7/2016 | Sturdivant | |
| 2016/0331260 A1 | 11/2016 | Han et al. | |

* cited by examiner

METHOD AND APPARATUS FOR TREATMENT OF CARDIOPULMONARY ARREST

CROSS-REFERENCE TO RELATED APPLICATION

The present Patent Application is a Continuation of U.S. application Ser. No. 15/892,864, filed Feb. 9, 2018, which claims benefit of U.S. Provisional Application No. 62/456,862, filed Feb. 9, 2017.

INCORPORATION BY REFERENCE

The disclosures of U.S. application Ser. No. 15/892,864, filed Feb. 9, 2018, and U.S. Provisional Application No. 62/456,862, filed Feb. 9, 2017, are hereby incorporated by reference for all purposes as if presented herein in their entireties.

FIELD

The present disclosure relates to methods and apparatus for treating cardiopulmonary arrest and, more particularly, for a method and apparatus to perform chest compression and defibrillation.

BACKGROUND

Cardiopulmonary resuscitation (CPR) was developed with external chest compressions in combination with mouth-to-mouth ventilation to form the basis of modern CPR. External defibrillation has since been incorporated into resuscitation guidelines. The key to survival from sudden cardiac arrest (SCA) are early recognition and treatment, specifically, immediate initiation of excellent CPR and early defibrillation.

The exact number of incidents of sudden cardiac arrest (SCA) in the United States is unknown, but estimates vary from 180,000 to over 450,000. In North America and Europe, the estimated incidents falls between 50 to 100 per 100,000 in the general population. The most common etiology of SCA is ischemic cardiovascular disease, resulting in the development of lethal arrhythmias. Resuscitation is attempted in up to two-thirds of people who sustain SCA.

Despite the development of cardiopulmonary resuscitation (CPR), electrical defibrillation, and other advanced resuscitative techniques, survival rates for SCA remain low. In the out-of-hospital setting, studies have reported survival rates of 1 to 6 percent. Three systematic reviews of survival-to-hospital discharge from out-of-hospital SCA reported 5 to 10 percent survival among those treated by emergency medical services (EMS) and 15 percent survival when the underlying rhythm disturbance was ventricular fibrillation (VF). Not performing CPR or low quality performance are important factors contributing to the poor outcomes. Multiple studies assessing both in-hospital and pre hospital performance of CPR have shown that trained healthcare providers consistently fail to meet basic life support guidelines.

The emphasis of treatment varies according to the phase of SCA the patient is suffering. In an electrical phase of SCA, which is defined as the first four to five minutes of arrest due to ventricular fibrillation (VF), immediate DC cardioversion is needed to optimize the survival of these patients. Performing excellent chest compressions while the defibrillator is readied also improves survival. In a hemodynamic or circulatory phase, which follows the electrical phase and consists of the period from 4 to 10 minutes after SCA, the patient can remain in VF. Early defibrillation remains critical for survival in patients found in VF. Excellent chest compressions should be started immediately upon recognizing SCA and continued until just before cardioversion is performed (i.e., charge the defibrillator during active compressions, stopping only briefly to confirm the rhythm and deliver the shock). CPR is resumed immediately after cardioversion is delivered.

Some of the mentioned problems of CPR performance are relatively well solved by mechanical devices for chest compressions. However, the known devices of this kind are too large and too heavy, which limits their use to specialized medical institutions. Their high prices are another barrier to their widespread use. Nevertheless, such devices still do not solve all the CPR problems described above. To determine if defibrillation is necessary, it is crucial to continuously record an electrocardiogram (ECG) of the patient's heart during CPR. ECG is recorded using electrodes or pads which are placed on the patient's bare skin. However, during chest compressions, regardless if they are performed by the rescuer or a mechanical device, ECG does not show the actual recording of the heart's electrical activity, but the artefacts produced by the movement of the chest. In order for an automated external defibrillator or the rescuer to analyze the heart rhythm, which is done every 2 minutes during CPR, chest compressions must be paused, resulting in complete termination of blood flow to the patient's vital organs. after each pause, it takes significant time of good quality chest compressions in order to build up the blood flow to the levels achieved before the pause.

The updated CPR guidelines recommend chest compressions at a rate of at least 100/minute. Studies have shown that higher compression rates are associated with higher survival rates. However, it is difficult for a layperson or first responder to apply rapid compressions at the recommended rate of 100/minute. Accordingly, it would be desirable to have a device that makes is easier to accomplish the rapid compressions at the recommended rate.

Further, it would be desirable to have an apparatus to address both the electrical and mechanical issues of CPR in an efficient manner.

Further, it would be desirable to provide an apparatus with a low cost disposable component in order to effectively avoid the spread of diseases through contact, which will also efficiently save time for medical professionals.

Further, it would be desirable to provide a method and an apparatus for addressing issues of electrical disturbance and efficient chest compression without delay or error by medical professionals.

Finally, it would be desirable that this device does not interfere with current diagnostic procedures, including but not limited to x-ray, percutaneous interventions, computed tomography or magnetic resonance imaging.

SUMMARY

Described herein is a cardiopulmonary resuscitation (CPR) device configured to perform automatic defibrillation and chest compressions on a patient. The CPR device can comprise a balloon configured to inflate/deflate. The CPR device can comprise a belt configured to securely strap around a chest of a patient. The CPR device can comprise a pair of electrode pads configured to deliver shock energy from a shock source. The CPR device can comprise a pulse oximeter sensor. The CPR device can be in electrical communication with a CPR defibrillator/ECG computer system configured to control the CPR device.

Various implementations described in the present disclosure can include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

DETAILED DESCRIPTION

The present disclosure can be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the disclosure is provided as an enabling teaching of the disclosure in its best, currently known aspect. To this end, those skilled in the relevant art will recognize and appreciate that many changes can be made to the various descriptions of the disclosure described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure.

As used throughout, the singular forms "a," "an" and "the" include plural referents unless the context clearly dictates otherwise. Thus, for example, reference to "an electrode" can include two or more such electrodes unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "can," unless specifically stated otherwise, or otherwise understood within the context as used, is generally intended to convey that certain aspects.

Figure 1:
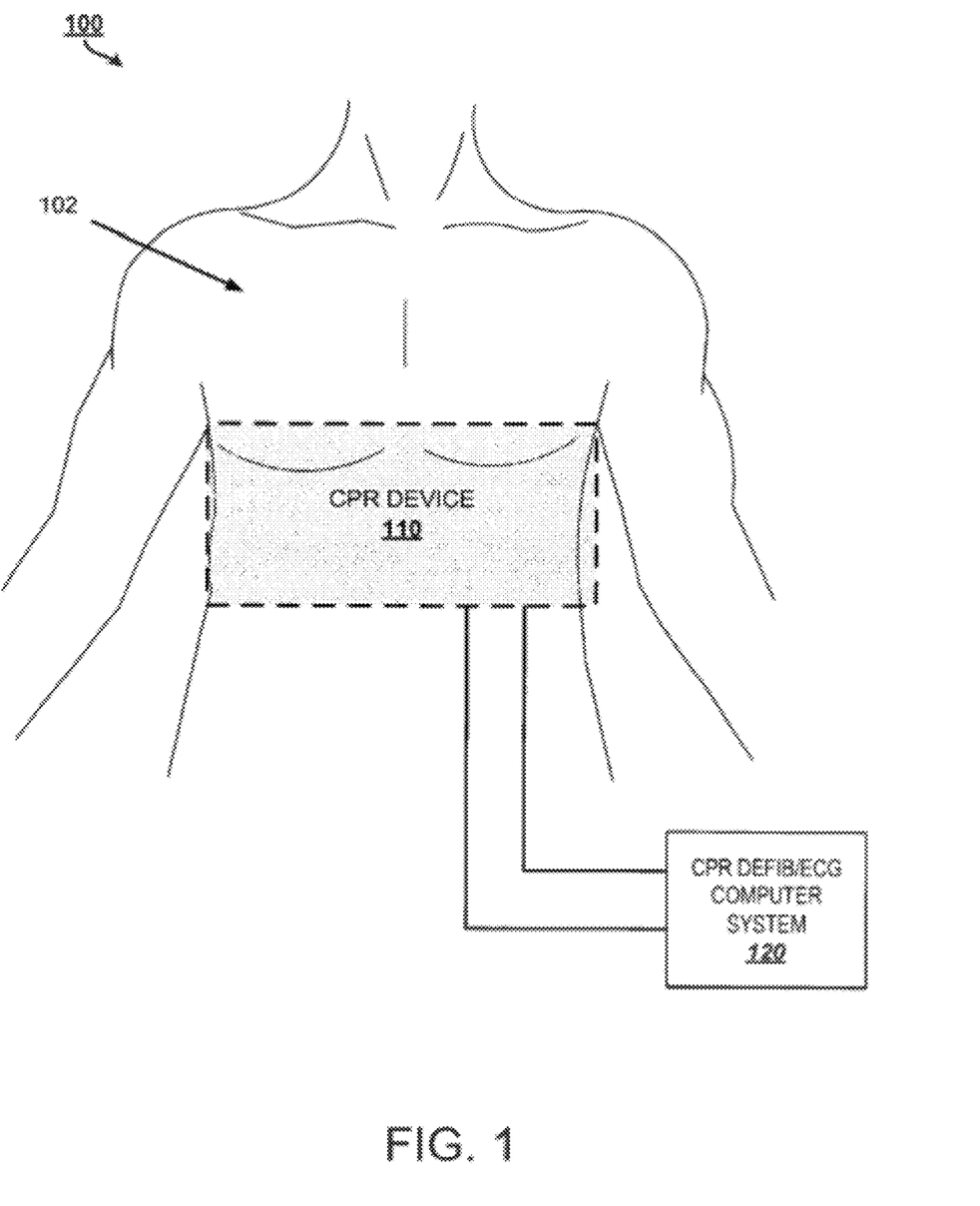
FIG. 1 is a schematic illustration of a non-limiting example of the preferred use of the cardiopulmonary resuscitation device.

Disclosed herein are methods and apparatus for treating cardio-pulmonary arrest. One aspect of an apparatus for treating cardiopulmonary arrest in accordance with the present disclosure is illustrated in the schematic diagram shown in FIG. 1 with a CPR system 100 comprising a CPR device 110 in communication with a CPR defibrillator/ECG computer system 120 to perform automatic chest compression and defibrillation. As illustrated, the CPR device 110 is positioned circumferentially about a lower portion of the pectorals of the patient and with at least a portion of an inward facing surface of the CPR device in contact with the skin of the patient 102.

Figure 2:
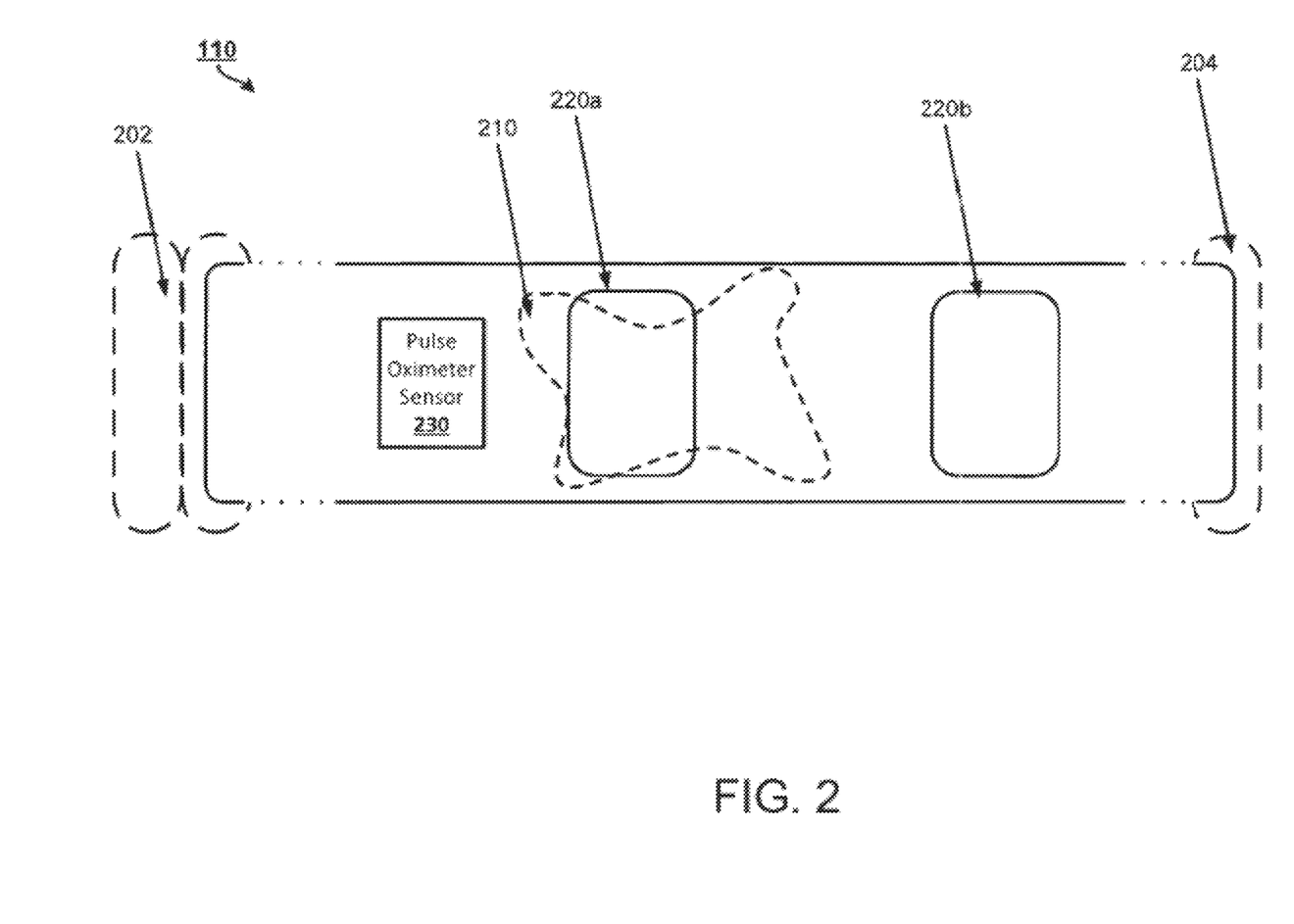
FIG. 2 is a schematic diagram illustrating a non-limiting example of a top elevational view of the cardiopulmonary resuscitation device.

As illustrated in the non-limiting exemplary device shown in FIG. 2, the CPR device 110 can be configured as a chest belt or strap, according to some aspects described herein. FIG. 2 is partial cross sectional view of the CPR device 110 displaying the inward facing surface that can be configured to circumferentially surround and contact a portion of the patient's chest when engaged. In one exemplary aspect, the CPR device 110 can comprise attachment means, such as illustrated exemplary buckles 202, 204, to secure the CPR device 110 in the desired position with respect to the patient 102 when in use. Optionally, it is contemplated that the attachment means can comprise Velcro straps or other known methods for securing a belt or strap to a person that can be configured to be adjustable to allow for different sizes of patients to be used by the CPR system disclosed herein.

In some aspects, the CPR device 110 can comprise a balloon 210. In this aspect, the balloon 210 can comprise an inflatable component that, when in a deflated position, is configured in a collapsed configuration shown in FIG. 2, and, when in an inflated position, is deployed in an expanded configuration (not shown), which is configured to move inwardly and away from the inward facing surface to provide a desired compression onto the portion of the chest of the patient that the balloon overlies to provide a desired compression onto the portion of the body that the balloon overlies. The inflatable component can comprise an elastic shell that expands when inflated. In one exemplary aspect, the shell can be made of polyethylene or any other suitable material. In some aspects, the balloon 210 can comprise a flexible air bladder that is operable coupled to a bulb pump that is in electrical communication with a balloon actuator module 416 for selective control of the inflation/deflation of the balloon actuator. In one aspect, the balloon actuator module 416 and the balloon 210 can comprise an automated balloon inflator system comprising generally an inflator and a communication device that is configured to selectively control the inflator to inflate a balloon to a predetermined size to simulate desired chest compressions.

In some aspects, the CPR device 110 can further comprise a pulse oximeter sensor 230 that is in electrical communication with a pulse oximeter module 424. As one skilled in the art will appreciate, a pulse oximeter is a device that is well known in the art for non-invasively determining the oxygen saturation of arterial blood. In the exemplary aspect, the CPR device 110 can be placed against the skin of the patient 102, thereby allowing the pulse oximeter sensor 230 to contact the skin of the patient when the CPR device 110 is properly secured to the patient 102. The pulse oximeter sensor 230 can be configured to transmit light at least two different wavelengths (such as, for example and without limitation) one wavelength in the red color spectrum, another wavelength in the infrared spectrum, and the like) through a portion of the patient's blood-perfused skin tissue. The exemplary red and infrared light wavelengths that are transmitted through the tissue are detected by a photodetector in the pulse oximeter sensor 230. It is known that the amount of light absorbed by a patient's blood-perfused skin tissue varies with the amount of oxygen in the blood, and also varies differently for red and infrared light wavelengths. The pulse oximeter module 424 is configured to compute blood oxygen saturation based on the changes in the two detected light levels of red and infrared light wavelengths between two discrete points in time or between a predetermined time interval.

In some aspects, the CPR device 110 can further comprise a plurality of electrode pads 220a,b, which can be positioned on the CPR device 110, preferably mounted to the inward facing surface of the belt, so that defibrillation of the patient can be selectively delivered to the patient via the plurality of electrode pads. Electrode pads 220a,b are structurally configured as known in the art to be conductively applied to a patient 102. It is contemplated that each electrode can be configured to conduct a defibrillation shock from a shock source 422 within the CPR defibrillator/ECG computer system 120 to a heart of patient 102 as controlled by the defibrillator module 420 in the CPR defibrillator/ECG computer system 120. The electrode pads 220a,b can also be configured to sense electrical activity of the heart of patient 102 and conduct that sensed electrical activity, in a form such as an ECG, to an output device 410 of the CPR defibrillator/ECG computer system 120. Alternatively or concurrently, the CPR device 110 can further comprise a plurality of ECG leads as known in the art that can be configured to be connected to patient 102 to conduct the electrical activity of heart of patient 102 to an ECG module 418. In one aspect, the ECG module 418 can be configured as known in the art to measure an ECG waveform of the heart of patient 102 as an indication that the patient 102 is experiencing an organized heartbeat condition or an unorganized heartbeat condition.

Figure 3:
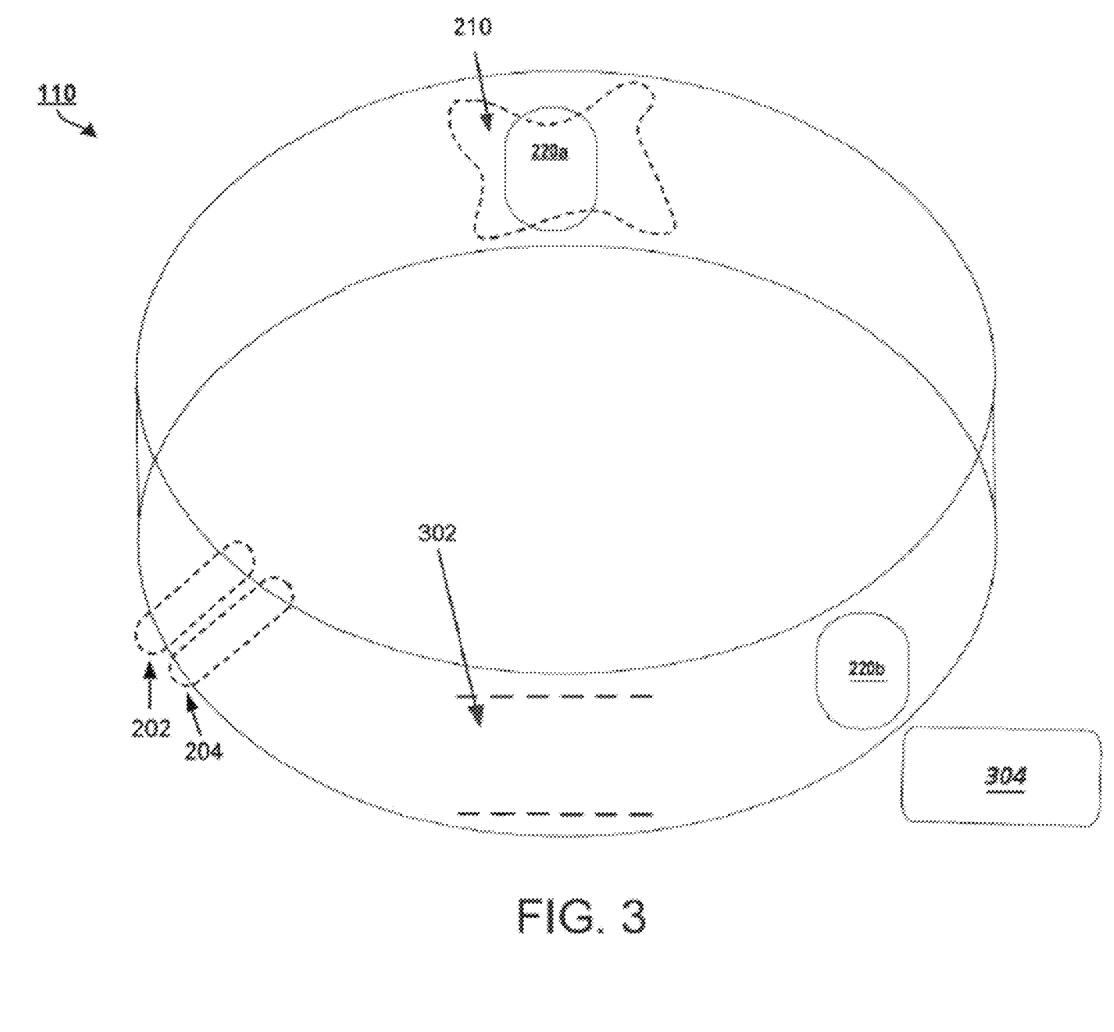
FIG. 3 is a schematic diagram illustrating a non-limiting example of a top elevational view of the cardiopulmonary resuscitation device.

As illustrated in the non-limiting exemplary device shown in FIG. 3, the CPR device 110 can be configured as a chest belt or strap, according to some aspects described herein. FIG. 3 is a top view of the entire CPR device 110, where attachment means, such as illustrated exemplary buckles 202, 204, are engaged securely around a patient 102 (not shown). In some aspects, the CPR device 110 can comprise a pocket 302 embedded in the back of the strap as shown in FIG. 3. In some aspects, the pocket 302 can comprise a separate layer of material attached to the CPR device 302.

Optionally, the pocket 302 can be configured to accept a support block 304 to provide support for a portion of the patient's back prior to the initiation of CPR, according to methods as will be further described herein. The support block 304 can comprise a substantially rigid material formed from wood, plastic, and the like, in order to provide support during CPR compressions. In a further aspect, the support block can also be substantially planar in shape.

Figure 4:
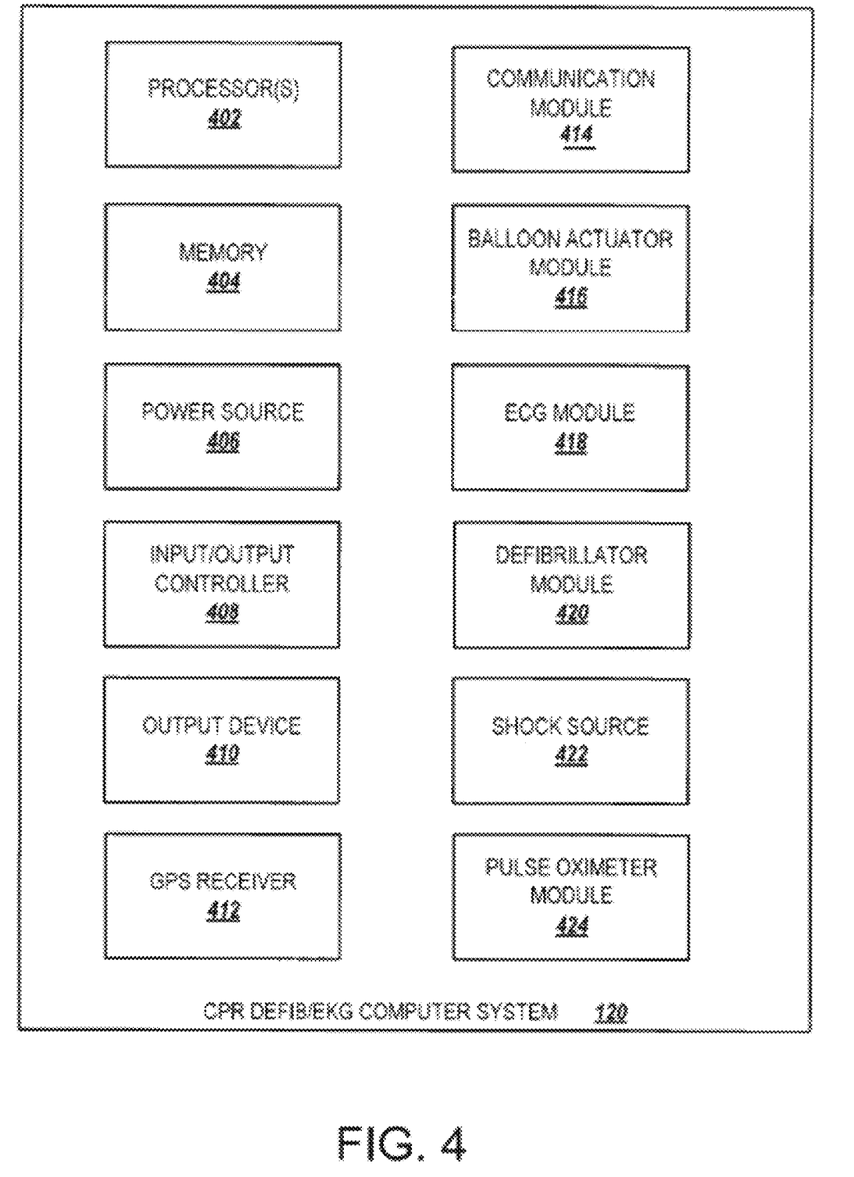
FIG. 4 is a schematic diagram illustrating a non-limiting example of an electronics assembly used in the CPR defibrillator/ECG computer system.

As illustrated in the non-limiting exemplary structure shown in FIG. 4, the electronic assembly of the CPR defibrillator/ECG computer system 120 can comprise at least a processor 402 (e.g., a microprocessor, a microcontroller, or another suitable programmable device), which that can represent standard programmable processors that perform arithmetic and logical operations necessary for the operation of the CPR defibrillator/ECG computer system 120.

For example and without limitation, the CPR defibrillator/ECG computer system 120 comprises memory 404 for storing data and or program instructions for execution by the processor 402. The memory 404 can comprise, for example, a read-only memory ("ROM"), a random access memory ("RAM"), an electrically erasable programmable read-only memory ("EEPROM"), a flash memory, a hard disk, an SD card, or another suitable magnetic, optical, physical, or electronic memory device. The processor 402 is connected to the memory 404 and executes software that is capable of being stored in the RAM (e.g., during execution), the ROM (e.g., on a generally permanent basis), or another non-transitory computer readable medium such as another memory or a disc. Additionally or alternatively, the memory 404 can be included in the processor 402. Exemplary software can include, for example, firmware, one or more applications, program data, one or more program modules, other executable instructions, and the like. It is contemplated that the processor 402 can be configured to retrieve from memory and execute, among other things, instructions related to the methods described herein.

The CPR defibrillator/ECG computer system 120 can also comprise an input/output controller 408 in electrical communication with the processor 402 for receiving and processing input from a number of input devices, such as a keyboard, a mouse, a touchpad, a touch screen, an electronic stylus, or other type of input device. Similarly, the input/output controller 408 can provide output to a display device, such as output device 410 as shown in FIG. 4. The output device 410 can comprise a computer monitor, a flat-panel display, a digital projector, or other type of output display device. It will be appreciated that the CPR defibrillator/ECG computer system 120 may not comprise all of the components shown in FIG. 4, can comprise other components that are not explicitly shown in FIG. 4, or can utilize an architecture completely different than that exemplarily shown in FIG. 4.

According to example aspects, the CPR defibrillator/ECG computer system 120 can comprise a power source 406 (e.g., a battery or an alternative power source) and a shock source 422. The shock source 422 can employ a high voltage capacitor bank (not shown) for storing a high voltage via a high voltage charger and a power supply upon activation. The shock source 422 can further employ a switching/isolation circuit (not shown) for selectively applying a specific waveform of an electric energy charge from the high voltage capacitor bank to electrode pads 220a,b as selectively controlled by the defibrillator module 420.

According to exemplary aspects, a communication module 414, a balloon actuator module 416, an ECG module 418, a defibrillator module 420, and a pulse oximeter module 424 can be configured to execute in the CPR defibrillator/ECG computer system 120. Each of the exemplary modules, data, and/or software can provide functionality for the CPR defibrillator/ECG computer system 120, when executed by processors of the CPR defibrillator/ECG computer system 120. The modules, data, and/or the software may or may not correspond to physical locations and/or addresses in the CPR defibrillator/ECG computer system 120 memory. In other words, the contents of each of the modules 414, 416, 418, 420, and 424 cannot be segregated from each other and can, in fact be stored in at least partially interleaved positions on the memory of the CPR defibrillator/ECG computer system 120.

While the example aspects in FIG. 4 present the communication module 414, the balloon actuator module 416, the ECG module 418, the defibrillator module 420, and the pulse oximeter module 424 as being separate, in other example aspects, the operations of these modules can be combined in any manner into fewer than the exemplarily presented modules. For example, the operations of the ECG module 418 and the defibrillator module 420 can be combined. In another example, all of the operations of the communication module 414, the balloon actuator module 416, the ECG module 418, the defibrillator module 420, and the pulse oximeter module 424 can be completed by a single module. Any other combination and consolidation of operations of the communication module 414, the balloon actuator module 416, the ECG module 418, the defibrillator module 420, and the pulse oximeter module 424 is contemplated herein.

In some aspects, the CPR defibrillator/ECG computer system 120 can be configured to connect to a network (e.g., a WAN, a LAN, or the like) via a communications module 414 to access other programs, software, or systems. In one non-limiting example, the communications module 414 can include a network interface, such as an Ethernet card or a wireless network card, that allows the CPR defibrillator/ECG computer system 120 to send and receive information over a network, such as a local area network or the Internet. Data communications can occur via a wireless local area network ("LAN") using any of a variety of communications protocols, such as Wi-Fi, Bluetooth, ZigBee, or the like. Additionally or alternatively, data communications can occur over a wide area network ("WAN") (e.g., a TCP/IP based network or the like).

In one example, the balloon actuator module 416 can be configured to control the balloon 210 for inflation/deflation to perform chest compressions for CPR. In some aspects, the balloon 210 can comprise a flexible air bladder that links to a bulb pump and the pump is controlled by the balloon actuator module 416 for inflation/deflation. In one aspect, the balloon actuator module 416 and the balloon 210 can comprise an automated balloon inflator system comprising generally an inflator and a communication device that instructs the inflator to inflate a balloon to a predetermined size to perform the chest compressions.

In one example, the ECG module 418 can be configured as known in the art to measure an ECG waveform of the heart of patient 102 as an indication patient 102 is experiencing an organized heartbeat condition or an unorganized heartbeat condition. The ECG waveform can then be displayed on the output device 410 for the user.

In another example, the defibrillator module 420 can be configured to control the shock source 422 by selectively applying a specific waveform of an electric energy charge from the high voltage capacitor bank to electrode pads 220a,b.

In a further example, the pulse oximeter module 424 can be configured to compute blood oxygen saturation based on the changes in the two detected light levels between two points in time as sensed by the pulse oximeter sensor 230. The blood oxygen saturation levels can then be displayed on the output device 410 for the user.

In the noted examples, it is contemplated that the modules described herein, e.g., the communication module 414, the balloon actuator module 416, the ECG module 418, the defibrillator module 420, and the pulse oximeter module 424 can be a combination of hardware and programming instructions. The programming instructions can be processor executable instructions stored on a tangible memory resource such as a computer-readable storage medium or other memory resource, and the hardware can include a processing resource for executing those instructions. Thus the memory resource can be said to store program instructions that when executed by the processing resource implement the modules described herein.

In some aspects, the CPR defibrillator/ECG computer system 120 can comprise a global positioning system (GPS) receiver 412 to indicate the device's location. In one aspect, the device location information can be transmitted via the communications module 414 to local 911 call centers as an automated mode of communication to emergency personnel. This can be beneficial if other modes of communication are unavailable at the time or at the location.

Figure 5:
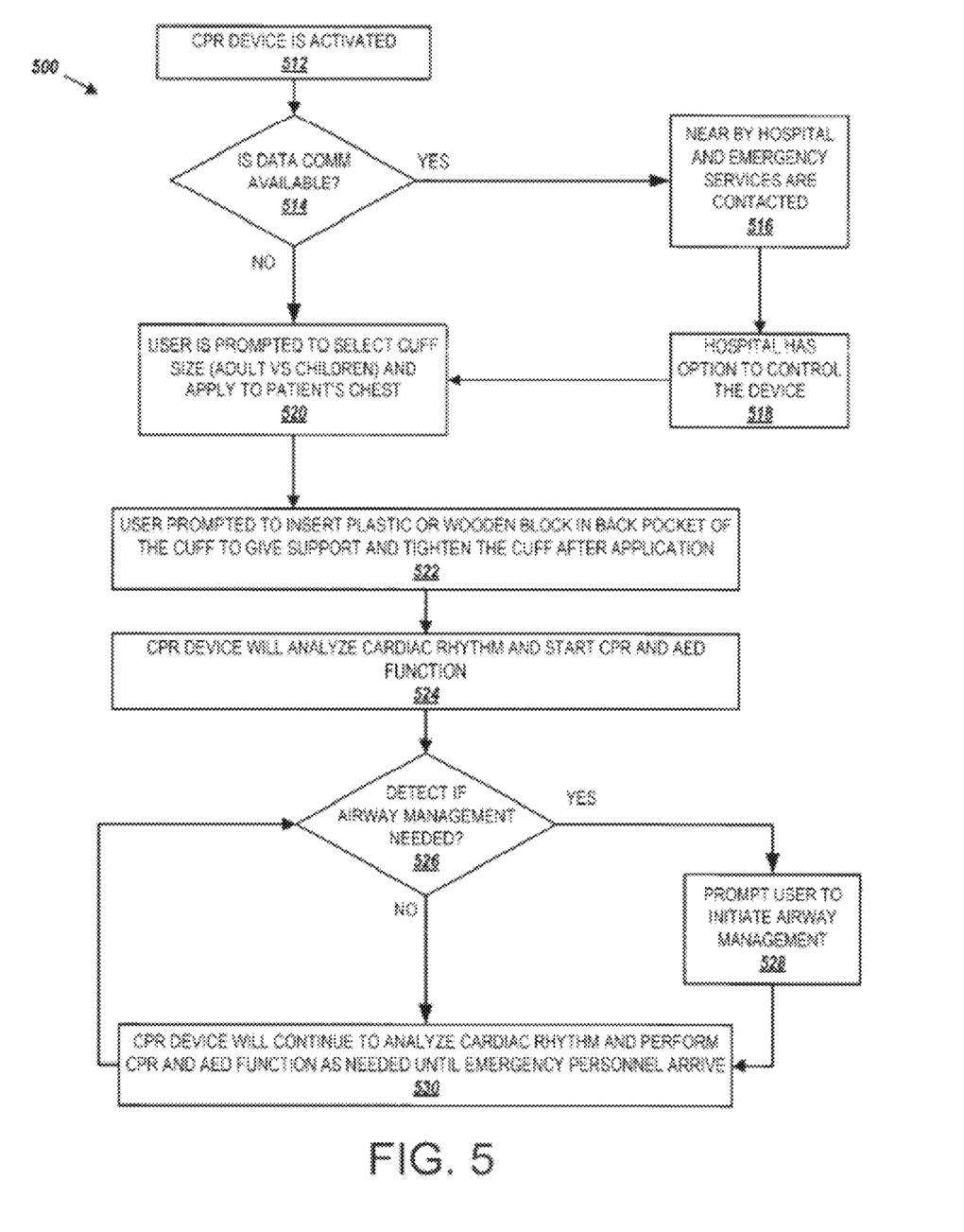
FIG. 5 is a schematic flow diagram illustrating one method for using the cardiopulmonary resuscitation device, according to some aspects of the present disclosure.

FIG. 5 shows one example of a method 500 for providing CPR to a person having a cardiac arrest or symptoms of cardiac rest from a bystander, user, hero, or the like, according to aspects of the present disclosure. The method 500 can allow a user to attach the portable CPR device 110 to a person they believe is having a cardiac emergency to aid in AED and CPR utilizing the CPR system 100.

At step 512, the CPR device 110 is activated. According to some aspects, the CPR system 100 is activated immediately after being detached from a wall where it resides. Optionally, the CPR system 100 can be activated once an "ON" button or a "START" button on either the CPR device 110 or CPR defibrillator/ECG computer system 120 is pressed. Next, in step 514, the CPR defibrillator/ECG computer system 120 determines if a data communication connection is available to communicate with emergency services and a nearby hospital via the communication module 414. In some aspects the emergency services, such as an ambulance center, and the hospital are programmed into the unit based on the location of each unit, or by an administrator with access to the CPR defibrillator/ECG computer system 120 diagnostics. If a data communication connection is determined to be available, at step 516, the CPR defibrillator/ECG computer system 120 contacts emergency services to pick up the patient 102 and the hospital to inform each entity of the situation. At step 518, the CPR defibrillator/ECG computer system 120 allows emergency services, such as a hospital or any preapproved entity, to access and control the CPR system 100.

At step 520, the user is prompted on the output device 410 to select a cuff size (adult or children) of the CPR device 110, and apply around the patient's chest. In some aspects, the output device 410 will show a picture or video tutorial to the user to ensure the CPR device 110 is properly on. The CPR defibrillator/ECG computer system 120 can detect whether the CPR device is properly engaged with the patient 102. The user is then prompted to insert a support block 304 into the back pocket 302 of the CPR device 110 and tighten the chest belt using the attachment means, such as the illustrated buckles 202, 204 (step 522).

At step 524, the CPR defibrillator/ECG computer system 120 will analyze the cardiac rhythm of the patient 102, determine if CPR and defibrillation is needed, and start CPR and/or AED functionality based on the cardiac rhythm.

At step 526, CPR defibrillator/ECG computer system 120 will continuously monitor and determine if airway management is needed. If airway management is not needed, the CPR defibrillator/ECG computer system 120 will proceed to step 530. If airway management is needed, the CPR defibrillator/ECG computer system 120 will prompt the user to initiate airway management (step 528). In some aspects, the CPR defibrillator/ECG computer system 120 will display a step-by-step guide on accomplishing this feat.

At step 530, the CPR defibrillator/ECG computer system 120 will continue to analyze the cardiac rhythm and perform CPR and AED functions via the CPR device 110 as needed until emergency personnel arrive and deactivate the CPR system 100. The CPR defibrillator/ECG computer system 120 will continuously monitor and determine if airway management is needed (526) during the CPR and/or AED functions.

It should be emphasized that the above-described aspects are merely possible examples of implementations, merely set forth for a clear understanding of the principles of the present disclosure. Many variations and modifications can be made to the above-described aspect(s) without departing substantially from the spirit and principles of the present disclosure. All such modifications and variations are intended to be included herein within the scope of the present disclosure, and all possible claims to individual aspects or combinations of elements or steps are intended to be supported by the present disclosure. Moreover, although specific terms are employed herein, as well as in the claims which follow, they are used only in a generic and descriptive sense, and not for the purposes of limiting the described disclosure, nor the claims which follow.

What is claimed is:

1. A cardiopulmonary resuscitation (CPR) device configured to perform automatic defibrillation to a heart of a patient and chest compressions on the patient, the CPR device comprising:
    a treatment system comprising:
        a CPR defibrillator module;
        an electrocardiogram (ECG) module; and
        a shock source in communication with the plurality of electrode pads;
    a belt configured to selectively circumferentially surround a portion of a chest of the patient, the belt having an inward facing surface that is configured to contact the portion of the patient's chest when engaged to the patient;
    a balloon mounted onto the inward facing surface of the belt, wherein the balloon is configured to selectively move inwardly and away from the inward facing surface to provide a desired compression onto the portion of the chest of the patient that the balloon overlies;
    a balloon actuator module in communication with the treatment system for selective control of a movement of the balloon; and
    a plurality of spaced electrode pads mounted to the inward facing surface of the belt, wherein the plurality of spaced electrode pads is in communication with the CPR defibrillator module in the treatment system for selective delivery of shock energy to the patient, wherein the shock source is configured to selectively apply a specific waveform of an electric energy charge from the shock source to the plurality of electrode pads as selectively controlled by the defibrillator module,
    wherein the belt defines a pocket in an outward facing surface of the belt; wherein the pocket is configured to underlie a back of the patient when the belt is engaged to the patient; and wherein the pocket is sized to selectively accept a support block to provide support for a portion of the back of the patient prior to actuation of the balloon actuator module.

2. The CPR device of claim 1, wherein the balloon comprises an inflatable component that comprises an elastic shell.

3. The CPR device of claim 2, wherein the balloon comprises a flexible air bladder operatively in communication with the balloon actuator module.

4. The CPR device of claim 1, wherein the balloon actuator module is configured to selectively inflate the balloon to a predetermined size to effect the desired chest compressions on the patient, wherein the balloon is configured to selectively move about and between an inflated position, such that the balloon is configured to provide the desired compression onto the portion of the chest of the patient that the balloon overlies, and a deflated position.

5. The CPR device of claim 4, wherein a first electrode pad of the plurality of electrode pads is configured to underlie the back of the patient and a second electrode pad of the plurality of electrode pads is configured to overlie a front portion of the chest of the patient when the belt is engaged to the patient.

6. The CPR device of claim 1, further comprising a pulse oximeter sensor mounted to the inward facing surface of the belt that is configured to contact skin of the patient when the belt is engaged about the patient, wherein the pulse oximeter sensor is in electrical communication with a pulse oximeter module in the treatment system for computing a blood oxygen saturation of the patient.

7. The CPR device of claim 1, wherein the plurality of electrode pads is configured to sense electrical activity of the heart of the patient and conduct sensed electrical activity to an output device of the treatment system.

8. The CPR device of claim 1, further comprising a plurality of ECG leads configured to be connected to the patient and to conduct sensed electrical activity of the heart of the patient to the ECG module of the treatment system.

9. The CPR device of claim 8, wherein the ECG module is configured to measure an ECG waveform of the heart of the patient to indicate a heartbeat condition.

10. The CPR device of claim 1, wherein the support block comprises a rigid material.

11. The CPR device of claim 1, wherein the treatment system comprises at least a processor connected to a memory, which is configured to execute software that perform arithmetic and logical operations for the operation of the treatment system.

12. The CPR device of claim 11, wherein the treatment system further comprises an input/output controller in electrical communication with the processor for receiving and processing input.

13. A method providing cardiopulmonary resuscitation (CPR) to a patient, the method comprising:
    activating the CPR device of claim 1;
    securing the CPR device about the portion of the patient's chest;
    analyzing a cardiac rhythm of the patient;
    determining whether CPR is needed;

determining whether defibrillation is needed;

initiating at least one of CPR or automated external defibrillator (AED) functionality based on the analyzed cardiac rhythm of the patient.

14. The method of claim 13, further comprising determining whether a data communication connection is available to communicate with emergency services via a communication module.

15. The method of claim 14, further comprising, when a data communication connection is determined to be available, contacting the emergency services to inform the emergency services of the patient.

16. The method of claim 15, further comprising allowing the emergency services to access and control the CPR device.

17. The method of claim 13, further comprising detecting whether the CPR device is properly engaged with the patient.

18. The method of claim 13, further comprising prompting a user on an output device to select a desired cuff size of the CPR device.

19. The method of claim 18, further comprising prompting the user to insert the support block into the pocket of the CPR device.

20. The method of claim 13, further comprising continuously monitoring and determining when airway management is needed.

21. The method of claim 20, further comprising, when the airway management is needed, prompting the user to initiate the airway management.

* * * * *